United States Patent [19]

Lapidus

[11] Patent Number: 5,543,148
[45] Date of Patent: Aug. 6, 1996

[54] STICK DELIVERY SYSTEM FOR TOPICAL APPLICATION OF A TREATMENT AGENT

[75] Inventor: Herbert Lapidus, Ridgefield, Conn.

[73] Assignee: Combe, Incorporated, White Plains, N.Y.

[21] Appl. No.: 274,098

[22] Filed: Jul. 12, 1994

[51] Int. Cl.$^6$ .............................. A61K 7/00; A61K 7/15; A61K 9/00; A61K 31/00

[52] U.S. Cl. .................... 424/401; 424/73; 424/DIG. 5; 424/DIG. 13; 514/772.3; 514/784; 514/817; 514/830; 514/858; 514/862; 514/887; 514/953; 514/844; 514/944

[58] Field of Search .................... 424/73, 401, DIG. 13, 424/DIG. 5; 514/817, 858, 862, 772.3, 784, 830, 887, 953, 844, 944

[56] References Cited

U.S. PATENT DOCUMENTS

| | | | |
|---|---|---|---|
| 2,732,327 | 1/1956 | Teller | 167/90 |
| 2,857,315 | 10/1958 | Teller | 167/90 |
| 4,226,889 | 10/1980 | Yuhas | 424/59 |
| 4,268,498 | 5/1981 | Gedeon et al. | 424/59 |
| 4,353,896 | 10/1982 | Levy | 424/195 |
| 4,478,853 | 10/1984 | Chaussee | 424/358 |
| 4,521,411 | 6/1985 | Koloff | 424/195.1 |
| 4,564,462 | 1/1986 | Watanabe et al. | 252/134 |
| 4,591,602 | 5/1986 | DeVillez | 514/463 |
| 4,702,916 | 10/1987 | Geria | 424/400 |
| 4,711,906 | 12/1987 | von Stetten et al. | 514/561 |
| 4,892,890 | 1/1990 | Damani | 514/784 |
| 5,114,717 | 5/1992 | Kuznitz et al. | 424/401 |
| 5,221,529 | 6/1993 | Tansley | 424/65 |

FOREIGN PATENT DOCUMENTS 56-53611  5/1981  Japan .

OTHER PUBLICATIONS

"External Analgesic Drug Products For Over–The–Counter Human Use", Federal Register, vol. 48. No. 27. Feb. 8, 1983.

*Primary Examiner*—James M. Spear
*Attorney, Agent, or Firm*—St. Onge Steward Johnston & Reens

[57] ABSTRACT

The invention presented relates to a stick delivery system for the topical application of a treatment agent. The inventive stick delivery system includes a solvent such as a polyhydric alcohol; a gelling agent which can be an alkali metal stearate, an alkali metal palmitate or mixtures thereof; and a treatment agent selected from the group consisting of an anesthetic, an antihistamine, an anti-inflammatory agent, an antifungal agent, or mixtures thereof.

16 Claims, No Drawings

STICK DELIVERY SYSTEM FOR TOPICAL APPLICATION OF A TREATMENT AGENT

TECHNICAL FIELD

The present invention relates to a stick delivery system for the topical application of a treatment agent. The treatment agent can be an anesthetic, an antihistamine, an anti-inflammatory agent and/or an antifungal agent, or mixtures of two or more. The treatment agents are effective for the treatment of skin conditions such as "razor burn"; poison ivy, insect bites, etc.; itching and inflammation; and athlete's foot or other fungal conditions.

BACKGROUND OF THE INVENTION

Creams, lotions and ointments for the treatment of skin conditions have been employed for many years. Typically, those creams, lotions and ointments are either inappropriate for the treatment for which they are used, or aesthetically unpleasing. For instance, razor burn, which is a colloquial expression for the areas of roughened, irritated and cut skin experienced after shaving, is a serious problem for women who shave a considerable portion of their bodies (legs, underarms and/or so-called "bikini" areas). Hand lotions or other emollient creams are often used in an attempt to soothe and cool these areas. However, such creams do not generally contain ingredients to encourage healing (such as an antipruritic like menthol) nor to adequately stem the discomfort (such as a topical anesthetic like lidocaine) and can be extremely messy when applied over large areas of skin.

Similarly, vehicles for the application of an antihistamine for insect bites, poison ivy and the like; an anti-inflammatory agent for itchy and inflamed skin; or an antifungal agent for athlete's foot can be messy and aesthetically unpleasing when applied as directed.

Although the prior art does include reference vehicles in which a local anesthetic such as lidocaine is present, such as U.S. Pat. No. 4,711,906 to von Stetten et al., such is for parenteral application. Topical preparations for analgesics are also known, such as those of U.S. Pat. No. 4,521,411 to Koloff and U.S. Pat. No. 4,353,896 to Levy, but they do not provide the degree of relief which can be provided by a topical anesthetic, especially since analgesics are generally applied for their activity below the skin surface, in muscles and joints.

What is desired, therefore, is a system for the topical delivery of a treatment agent effective for easing the discomfort of razor burn, the sting and itching of insect bites or poison ivy (or the like), the irritation of itchy and inflamed skin, or the nuisance of athlete's foot, which effectively delivers the treatment agent in a non-messy, aesthetically pleasing vehicle.

DISCLOSURE OF INVENTION

The present invention provides such a system, in an inventive stick delivery system effective for the topical application of a treatment agent selected from the group consisting of a topical anesthetic, an antihistamine, an anti-inflammatory agent, an antifungal agent, and mixtures thereof. The stick delivery system includes a solvent which comprises a dihydric or polyhydric alcohol (or mixtures thereof), a gelling agent which comprises an alkali metal stearate or an alkali metal palmitate (or mixtures thereof) and, in a preferred embodiment, water.

Most preferably, the inventive stick delivery system comprises about 70% to about 80% by weight of the solvent, about 5% to about 12% by weight of the gelling agent, about 1% to about 10% by weight of the treatment agent, and 5% to about 23.5.% by weight of water. In addition, an antipruritic agent, at a level of about 0.25% to about 5%, more preferably about 0.5% to about 1.5%, by weight, can be included when its combination with the treatment agent employed is acceptable.

The nature of the treatment agent, or combination of treatment agents, to be employed depends upon the condition or conditions for which relief is sought. For instance, where it is razor burn to be addressed, the treatment agent is advantageously a topical anesthetic which, when combined with the activity of an antipruritic agent, provides a degree of relief not available from the commonly used hand lotions or emollient creams. Where insect bites, poison ivy or like conditions are addressed, the treatment agent should advantageously be an antihistamine which functions to reduce the itching and discomfort. When the problem to be addressed is itching and inflamed skin, an anti-inflammatory agent is advantageously employed in the stick delivery system. And where athlete's foot (or like fungal condition) is the problem, an antifungal agent is the preferred treatment agent. In addition, as noted, where more than one of these conditions exists, it may be possible that the treatment agents can be combined in the inventive stick delivery system for effective relief.

In a preferred embodiment of the present invention, the skin condition to be addressed is razor burn, which can be a cause of extreme discomfort, especially to a women who shaves a large amount of her body i.e., legs, underarms and "bikini" area. When it is razor burn to be addressed, the treatment agent included in the stick delivery system is a topical anesthetic, which is a topically applied composition which relieves pain by depressing cutaneous sensory receptors. Exemplary of topical anesthetics which can be employed in this invention are benzocaine (ethyl-p-aminobenzoate hydrochloride), butamben (butyl aminobenzoate), dibucaine (2-n-butoxy-N-( 2-diethylaminoethyl)-cinchoninamide), dimethisoquin hydrochloride (3-butyl-l-(2-dimethylaminoethoxy) isoquinoline hydrochloride), dyclonine hydrochloride (4'-butoxy-3-piperidinopropiophenone hydrochloride), lidocaine (α-diethyl-aminoaceto-2,6-xylidide), lidocaine hydrochloride, pramoxine hydrochloride (4-n-butoxyphenol ether hydrochloride), tetracaine (4-n-butylaminobenzoate), and tetracaine hydrochloride, as well as mixtures and combinations thereof when appropriate. Most preferred among the topical anesthetics is lidocaine.

The topical anesthetic should be included in the stick delivery system of the present invention in an amount effective to relieve the pain of razor burn. More particularly, the topical anesthetic should be present in an amount of about 1% to about 10% by weight, more preferably, especially when lidocaine is the topical anesthetic employed, about 1% to about 6% by weight.

It can also be advantageous, when the treatment agent is a typical anesthetic, to include an antipruritic agent with the treatment agent for most effective relief. The antipruritic agent included in the stick delivery system of the present invention is one which is effective, when topically applied, to relieve itching, generally by depressing cutaneous sensory receptors. Exemplary of antipruritic agents which can be used herein are camphor, camphorated metacresol, juniper tar, menthol, phenol, phenolate sodium and resorcinol, present in amounts effective for antipruritic activity. Menthol is preferred (either-l-menthol, which is naturally occurring menthol, or racemic (dl) menthol, which can be natural or synthetic menthol), because, in addition to its antipruritic activity, menthol imparts a desirable "medicinal" odor to the stick delivery system.

It is highly preferred that the antipruritic agent employed provide antipruritic activity without also providing analgesic activity, which can in certain circumstances be counterproductive. For instance, menthol exhibits analgesic activity (that is, sub-dermal warmth and surface redness) at levels as low as 1.25%, although it is generally considered necessary for it to be present at levels of at least about 2.5%, and even 5%, for effective analgesic activity. Analgesic activity should be avoided, since warmth and redness will tend to exacerbate the irritation in conditions like razor burn, where warmth and redness are among the symptoms of the condition.

When menthol is used as the antipruritic agent, therefore, it should be present at a level of up to about 1.5% by weight of the inventive stick delivery system. The minimum level of menthol for observed antipruritic activity is about 0.25%. More preferably, menthol is present as the antipruritic agent at a level of about 0.8% to about 1.1% by weight.

In another embodiment of this invention, when the skin condition to be addressed is one where moisture is present as a result of skin breakage, such as insect bites, poison ivy, and the like (such as poison sumac, poison oak, etc.), the treatment agent should preferably be an antihistamine, which is a synthetic composition which can prevent or counteract the action of excess histamine in body tissues. Suitable antihistamines include diphenhydramine (2-diphenylmethoxy-N,N-dimethylethanamine), diphenhydramine hydrochloride, tripelennamine (N,N-dimethyl-N'-(phenylmethyl)-N'-2-pyridinyl-1,2-ethanediamine), tripelennamine hydrochloride, and mixtures or combinations of these (when appropriate). The antihistamine can be employed in the stick delivery system in the amount of about 1% to about 3.5% by weight, preferably about 1% to about 2.5% by weight.

The stick delivery system of the present invention can also be used to address itching and inflammation of the skin. In this instance, the treatment agent should be an anti-inflammatory agent, including over-the-counter agents such as hydrocortisone (17-hydroxycorticosterone) and hydrocortisone acetate and prescription agents such as betamethasone (9-fluoro-11,17,21-trihydroxy-16-methylpregna-1,4-diene-3,20-dione) and fluocinolone acetonide (6,9-difluoro-11,21-dihydroxy-16,17-[(1-methylethylidine) bis(oxy)]-pregna-1,4-diene-3,20-dione). Mixtures of these can also be used when appropriate. The anti-inflammatory agent is used at a level of about 0.01% to about 3.5% by weight, more preferably about 1% to about 2.5% by weight.

Where the condition to be addressed with the stick delivery system is athlete's foot, or other fungal conditions, the treatment agent employed is an antifungal agent, in yet another embodiment of the invention. Typical antifungal agents for this purpose include tolnaftate (o-2-naphthyl-meta-N-dimethylthiocarbanilate), miconazole (1-[2-(2,4-dichlorophenyl)-2-[(2,4-dichlorophenyl) methoxy]ethyl]-1H-imidazole) and chlortrimazole, present at levels of about 1% to about 2% by weight.

In addition, it is possible to include more than one treatment agent in the stick delivery system, to address more than one skin condition at a time. In this case, the treatment agents incorporated in the stick delivery system are included at levels within their individual preferred ranges. However, it is preferred that the total level of treatment agent in the inventive stick delivery system not exceed about 10% by weight.

In order to provide an appropriate carrier for the treatment agent being applied by the stick delivery system of the present invention, a combination of components must be provided such that the antipruritic agent and treatment agent are "carried" in an aesthetically desirable, non-messy vehicle. Since the intended areas of the skin for application of the delivery system of this invention are often exposed, a messy, non-aesthetically pleasing vehicle will defeat its purpose, since it will discourage use.

To that end, the vehicle employed is one which comprises a solvent which includes a dihydric or polyhydric alcohol or mixtures thereof, where the solvent is present at a level of about 70% to about 80% by weight of the stick delivery system, more preferably about 71 to about 74% by weight of the stick delivery system; and a gelling agent comprising an alkali metal stearate or palmitate, present at a level of about 5% to about 12% by weight of the stick delivery system preferably about 6% to about 8% by weight. Water may also be included, when needed to make up the balance of the vehicle, at a level of about 5% to about 24% by weight, preferably about 10% to about 15% by weight, of the stick delivery system.

As noted, the solvent used in the inventive stick delivery system comprises a dihydric alcohol, that is, a diol or alcohol having two hydroxyl groups (collectively referred to as "glycols") and/or a polyhydric alcohol, that is, a polyol or alcohol having three or more hydroxyl groups (collectively referred to as "glycerols" when three hydroxyl groups are present and "sugar alcohols" when more than three hydroxyl groups are present). Most advantageously, the solvent is made up entirely of dihydric and/or polyhydric alcohols. Typically employed among the alcohols are propylene glycol, dipropylene glycol, hexylene glycol, sorbitol, polyethylene glycol, glycerol, a monoalkyl ether of diethylene glycol and derivatives thereof, a dialkyl ether of diethylene glycol and derivatives thereof (the mono- and dialkyl ethers of diethylene glycol, and their derivatives are commercially available under the tradename Carbitol), tri-methylene glycol, 1,3-butane diol, 1,4-butane diol, and mixtures thereof.

In addition to the glycols and polyols listed above, it is possible to add various other adjuvants or co-solvents in order to enhance the solvency of actives, i.e., skin conditioners, skin wetting agents, etc. These materials are cosmetic grade esters and ethers that can be added to the stick. The only criterion for these adjuvants is that they be soluble in the glycols or polyols used. Exemplary are triglyceryl acetate, triethyl citrate, polyoxyethylene-2-oleate.

The gelling agent employed can be any agent suitably compatible with the solvent and capable of forming a translucent or transparent gelled stick, with a non-waxy and non-greasy feel when applied to human skin. The preferred gelling agents are alkali metal stearates, alkali metal palmitates, or mixtures thereof. Most preferred are sodium stearate, sodium palmitate, potassium stearate and potassium palmitate, as well as combinations of any two or more of them.

In addition to the aforementioned ingredients, it should also be noted that the following ingredients may also be included in the inventive stick delivery system, as desired: coloring agents, fragrances, conditioners, moisturizers, surfactants, antioxidants, preservatives, etc.

The components used to prepare the inventive stick delivery system are combined so as to produce a stick product having an antipruritic agent and treatment agent uniformly dispersed throughout. Typically, the delivery system is prepared by combining the treatment agent, solvent, gelling agent, and water, when present, and heating the combination to about 60° C. to about 80° C., more preferably about 67° C. to about 77° C., with stirring, until a uniform mixture is obtained. The antipruritic agent (when employed) is then added with mixing, and the mixture poured into the desired mold and allowed to cool.

The inventive stick delivery system provides a solid dosage form which can replace conventional creams, ointments, lotions, etc., which can be messy and discontinuous when allowed to dry. The solid stick delivery system disclosed and claimed herein provides a uniform deposit in a thin nonmessy layer that adheres to the skin, providing a reservoir of active ingredients for relief and cure of various skin conditions.

The following example further illustrates and explains the invention, but is not considered limiting.

EXAMPLE

A stick delivery system for the treatment of razor burn is prepared by combining 8% by weight sodium stearate, 72% by weight propylene glycol, 4% by weight lidocaine, and 15% by weight water, and heating to 70° C. to 75° C. while stirring, until a uniform mixture is obtained. Menthol (1%) is then added and the mixture stirred, after which it is poured into a mold delivery system to cool. After cooling, the stick is ready for usage.

The thusly prepared stick delivery system is then applied to skin immediately after shaving, and resulting in substantial relief of razor burn.

The above description is for the purpose of teaching the person of ordinary skill in the art how to practice the present invention and it is not intended to detail all of those obvious modifications and variations of it which will become apparent to the skilled worker upon reading the description. It is intended, however, that all such obvious modifications and variations be included within the scope of the present invention which is defined by the following claims. The claims are meant to cover the claimed elements and steps in any arrangement or sequence which is effective to meet the objectives there intended, unless the context specifically indicates the contrary.

I claim:

1. A stick delivery system for the topical application of a treatment agent, the stick delivery system comprising about 70% to about 80% by weight of a solvent which comprises a dihydric alcohol, polyhydric alcohol or mixtures thereof; about 5% to about 12% by weight of a gelling agent which comprises an alkali metal stearate, an alkali metal palmitate or mixtures thereof; an antipruritic which comprises menthol present at a level of about 0.5% to about 1.1% by weight; about 1% to about 10% by weight of a treatment agent selected from the group consisting of an anesthetic, an antihistamine, an anti-inflammatory agent, an antifungal agent, or mixtures thereof; and about 5% to about 23.5% water.

2. A stick delivery system for the topical application of a treatment agent, the stick delivery system comprising about 70% to about 80% by weight of a solvent which comprises a dihydric alcohol, polyhydric alcohol or mixtures thereof; about 5 % to about 12% by weight of a gelling agent which comprises an alkali metal stearate, an alkali metal palmitate or mixtures thereof; about 5% to about 23.5% by weight of water; and about 1% to about 10% by weight of a treatment agent selected from the group consisting of a. an anesthetic selected from the group consisting of benzocaine, butamben, dibucaine, dimethisoquin, dyclonine, lidocaine, pramoxine, tetracaine, and mixtures thereof;

b. an antihistamine selected form the group consisting of diphenhydramine, diphenhydramine hydrochloride, tripelennamine, tripelennamine hydrochloride, and mixtures thereof;

c. an anti-inflammatory agent selected from the group consisting of hydrocortisone, hydrocortisone acetate, betamethasone, fluocinalone and mixtures thereof;

d. an antifungal agent selected from the group consisting of tolnaftate, miconazole, clotrimazole and mixtures thereof; and e. mixtures thereof.

3. The stick delivery system of claim 1, wherein the dihydric or polyhydric alcohol is selected from the group consisting of propylene glycol; dipropylene glycol; hexylene glycol; sorbitol; polyethylene glycol; glycerol; a monoalkyl ether of diethylene glycol; a dialkyl ether of diethylene glycol; tri-methylene glycol; 1,3-butane diol; 1,4-butane diol; and mixtures thereof.

4. The stick delivery system of claim 1, wherein the gelling agent comprises sodium stearate; potassium stearate; sodium palmitate; potassium palmitate; or mixtures thereof.

5. The stick delivery system of claim 2, which further comprises an antipruritic agent.

6. The stick delivery system of claim 5, wherein the antipruritic agent is present at a level of about 0.25% to about 5% by weight.

7. The stick delivery system of claim 6, wherein the antipruritic agent comprises menthol.

8. The stick delivery system of claim 7, wherein menthol is present at a level of about 0.5% to about 1.1% by weight.

9. A method for the treatment of razor burn, which comprises preparing a stick delivery system comprising about 70% to about 80% by weight polyhydric alcohol; about 5% to about 12% by weight alkali metal stearate, alkali metal palmitate or mixtures thereof; about 0.25% to about 5% by weight antipruritic agent; about 3% to about 6% by weight anesthetic; and 5% to about 24% water; and applying the stick delivery system to skin having razor burn.

10. The stick delivery system of claim 2, wherein the topical anesthetic is present at a level of about 1% to about 6% by weight.

11. A method for the treatment of insect bites and poison ivy, which comprises preparing a stick delivery system comprising about 70% to about 80% by weight polyhydric alcohol; about 5% to about 12% by weight alkali metal stearate, alkali metal palmitate or mixtures thereof; about 1% to about 3.5 % by weight antihistamine; and about 5 % to about 24 % water; and applying the stick delivery system to skin having insect bites or poison ivy.

12. The stick delivery system of claim 2, wherein the antihistamine is present at a level of about 1% to about 3.5% by weight.

13. A method for the treatment of itching and inflammation, which comprises preparing a stick delivery system comprising about 70% to about 80% by weight polyhydric alcohol; about 5% to about 12% by weight alkali metal stearate, alkali metal palmitate or mixtures thereof; about 1% to about 3.5% by weight anti-inflammatory agent; and 5% to about 24% water; and applying the stick delivery to itchy or inflamed skin.

14. The stick delivery system of claim 2, wherein the anti-inflammatory agent is present at a level of about 1% to about 3.5% by weight.

15. A method for the treatment of athlete's foot, which comprises preparing a stick delivery system comprising about 70% to about 80% by weight polyhydric alcohol; about 5% to about 12% by weight alkali metal stearate, alkali metal palmitate or mixtures thereof; about 1% to about 2% by weight anti-fungal agent; and 5% to about 24% water; and applying the stick delivery system to skin having athlete's foot.

16. The stick delivery system of claim 2, wherein the antifungal agent is present at a level of about 1% to about 2% by weight.

\* \* \* \* \*